United States Patent [19]

Akatsu et al.

[11] Patent Number: 4,982,042
[45] Date of Patent: Jan. 1, 1991

[54] PROCESS FOR MANUFACTURE OF OLEFIN OLIGOMER

[75] Inventors: Makoto Akatsu; Tatsuya Kawamura, both of Tokuyama, Japan

[73] Assignee: Idemitsu Petrochemical Co., Ltd., Tokyo, Japan

[21] Appl. No.: 420,573

[22] Filed: Oct. 12, 1989

[30] Foreign Application Priority Data

Oct. 17, 1988 [JP] Japan ................................ 63-259397
Jan. 20, 1989 [JP] Japan ..................................... 1-9913

[51] Int. Cl.$^5$ ..................... C10L 1/16; C07C 15/12; B01J 21/02
[52] U.S. Cl. .................................. 585/510; 585/525; 585/902; 585/906; 502/203
[58] Field of Search ............... 585/510, 525, 502, 906; 502/203

[56] References Cited

U.S. PATENT DOCUMENTS

| | | | |
|---|---|---|---|
| 3,780,128 | 12/1973 | Shubkin | 585/525 |
| 3,929,749 | 12/1975 | Cooper et al. | 502/32 |
| 4,213,001 | 7/1980 | Madgavkar et al. | 585/525 |
| 4,239,930 | 12/1980 | Allphin et al. | 585/525 |
| 4,263,467 | 4/1981 | Madgavkar et al. | 585/525 |
| 4,365,105 | 12/1982 | Morganson et al. | 585/525 |
| 4,384,162 | 5/1983 | Vogel et al. | 585/525 |
| 4,429,177 | 1/1984 | Morganson et al. | 585/525 |
| 4,433,197 | 2/1984 | Vogel et al. | 585/525 |

OTHER PUBLICATIONS

"Boron Trifluoride and its Derivatives" Booth et al., John Wiley and Sons (1949); pp. 225-226.

Primary Examiner—Curtis R. Davis
Attorney, Agent, or Firm—Hidaka and Benman

[57] ABSTRACT

A process for the manufacture of an olefin oligomer, comprising the steps of polymerizing an olefin monomer in the presence of boron trifluoride and a boron trifluoride-alcohol complex as catalysts, to prepare a first oligomerization product, and then carrying out one of following steps (a) to (c): (a) removing boron trifluoride from the above first product by (i) placing the product under a reduced pressure, (ii) blowing an inert gas into the product, or (iii) heating the product at a relatively low temperature, to thereby prepare a second oligomerization product, and then subjecting the second product to a precipitation treatment to separate the boron trifluoride-alcohol complex therefrom, (b) heating the above first product at a relatively elevated temperature to recover boron trifluoride, or (c) centrifuging the above first product to recover the boron trifluoride-alcohol complex. These steps allow the catalysts to be recovered while maintaining the activity thereof at a desired level.

8 Claims, No Drawings

PROCESS FOR MANUFACTURE OF OLEFIN OLIGOMER

BACKGROUND OF THE INVENTION

1. Field of the Invention

The present invention relates to a process for the manufacture of an olefin oligomer, particularly, an olefin oligomer suitable for use as synthetic lubricant base fluids wherein catalysts can be recovered while maintaining the activities thereof.

2. Description of the Related Art

An olefin oligomer prepared by polymerizing an olefin, particularly an alpha-olefin having 6 to 12 carbon atoms, is useful as synthetic lubricant base fluids.

In a known process for the production of such an alpha-olefin oligomer, the polymerization is carried out by using boron trifluoride and a boron trifluoride-alcohol complex as catalysts. Reference is made to Japanese Examined Patent Publications (KOKOKU) No. 59.53244, No. 60-37159, and No. 61-326, and U.S. Pat. No. 3,382,291 and U.S. Pat. No. 3,780,128.

The above conventional process for the production of the olefin oligomer using the above-mentioned catalysts is widely used, because not only the oligomer can be obtained in a high yield, but also the reaction can be controlled to obtain a desired oligomer, and the like.

In the above conventional process, however, the polymerization product is treated by adding an alkaline or water to deactivate and discard the catalysts. Hitherto, there was no satisfactory process for recovering the catalysts. For example, this can be done by allowing the polymerization product to stand, whereby the catalysts are separated therefrom and recovered. However, the product must be allowed to stand for a long time, and the activity of the recovered catalysts is lowered.

SUMMARY OF THE INVENTION

After intensive research to determine a means of remedying the above disadvantages, the inventors of the present invention found that the catalysts for this oligomerization can be recovered by simple procedures while maintaining the activity thereof.

Accordingly, the object of the present invention is to provide a process for efficiently manufacturing an olefin oligomer, while recovering the catalysts having a strong activity by simple procedures.

Other objects and advantages of the present invention will be apparent from the following description.

In accordance with the present invention, there is provided a process for the manufacture of an olefin oligomer, comprising the steps of:

polymerizing an olefin monomer in the presence of boron trifluoride and a boron trifluoride-alcohol complex as catalysts, to prepare a first oligomerization product; and then carrying out one of following steps (a) to (c);

(a) removing boron trifluoride from the above first product by (i) placing the product under a reduced pressure, (ii) blowing an inert gas into the product, or (iii) heating the product at a relatively low temperature, to thereby prepare a second oligomerization product, and then subjecting the second oligomerization product to a precipitation treatment to separate the boron trifluoride-alcohol complex therefrom, (b) heating the above first product at a relatively elevated temperature to recover boron trifluoride, or (c) centrifuging the above first product to recover the boron trifluoride-alcohol complex.

DESCRIPTION OF THE PREFERRED EMBODIMENTS

In the present invention, there is no restriction on the olefin monomer used, and any olefin monomer having 2 or more carbon atoms, for example, alpha-olefin monomer, inner olefin monomer, and a mixture thereof, may be used. Desirably, an alpha-olefin monomer having 4 to 32, preferably 6 to 15, carbon atoms is used.

The olefin monomer is polymerized in the presence of catalysts, i.e., boron trifluoride and boron trifluoride-alcohol complex, to produce an olefin oligomer.

The boron trifluoride and boron trifluoride-alcohol complex may be employed in the same proportions as in the conventional process. A molar ratio of the boron trifluoride/boron trifluoride-alcohol complex is preferably at least 0.01, more preferably 0.02 to 0.3.

There is no limit to the amount of the catalysts used, but this amount is preferably 0.05 to 10.0% by weight, more preferably 0.1 to 5.0% by weight, with respect to the weight of the olefin monomer used.

As an alcohol forming the complex with boron trifluoride, there may be mentioned a lower alcohol such as methyl alcohol, ethyl alcohol, n-butyl alcohol, or the like.

Polymerization may be carried out without the use of a solvent, but, if desired, a halogenated hydrocarbon such as carbon tetrachloride, chloroform or methyl chloride, or a saturated hydrocarbon such as pentane, hexane, heptane, or the like, may be employed as the solvent.

The polymerization conditions are not critical, but usually the polymerization temperature is $-20°$ to $90°$ C., preferably $0°$ to $50°$ C., and the pressure of the boron trifluoride is preferably 0 to 35 kg/cm$^2$G, more preferably, 0.05 to 5 kg/cm$^2$G.

The polymerization time is preferably 0.25 to 8 hours, more preferably 0.5 to 4 hours.

In the present invention, the olefin monomer is polymerized as above to produce a first oligomerization product, which is then treated by one of the above-mentioned steps (a) to (c).

STEP (a)

The first oligomerization product is subjected to a moderate treatment to remove or recover boron trifluoride other than the boron trifluoride forming the complex together with alcohol. The moderate treatment may be performed by (i) placing the first product under a reduced pressure, for example, 0.1 to 200 mmHg, (ii) blowing an inert gas, such as nitrogen, argon, or helium gas, into the first product, or (iii) heating the first product at a relatively low temperature, to thereby prepare a second oligomerization product. The term "relatively low temperature" as used herein means the temperature at which the boron trifluoride-alcohol complex is not pyrolytically decomposed to form boron trifluoride and alcohol, and is preferably less than about 80° C., more preferably about 40° to 60° C. The recovered boron trifluoride may be used as the catalyst for the polymerization of the olefin oligomer, without subsequent treatment.

The second product is then subjected to a precipitation treatment to separate or recover the boron trifluoride-alcohol complex therefrom. The precipitation treatment may be performed, for example, by merely allowing the second product to stand at a room temperature or about 20° C. under an atmospheric pressure, for about 1 to about 8 hours.

The recovered boron trifluoride-alcohol complex exhibits substantially the same level of activity as that of the original activity, and may be used for the polymerization without subsequent treatment.

STEP (b)

The first product may be heated at a relatively elevated temperature. The term "relatively elevated temperature" as used herein means the temperature at which the boron trifluoride-alcohol complex is pyrolytically decomposed to boron trifluoride and alcohol, and is preferably about 80° C. or more, more preferably about 85° to about 200° C. In this step (b), not only the boron trifluoride not forming the complex, but also the boron trifluoride forming the complex are removed or recovered from the first product. The recovered boron trifluoride may be used as the catalyst for the polymerization of the olefin oligomer.

In the step (b), preferably the first product is subjected to one of the moderate treatments (i) to (iii) as in the step (a), before heating at the relatively elevated temperature. When the boron trifluoride not included in the complex is removed from the first product under a moderate condition, the catalyst system comprising the boron trifluoride and boron trifluoride-alcohol complex is deactivated. Accordingly, the first product is not further polymerized during this moderate treatment and the subsequent heating treatment at the relatively elevated temperature, and as a result, an oligomer having properly controlled properties can be produced.

STEP (c)

The first product may be centrifuged to remove or recover the boron trifluoride-alcohol complex.

The centrifuging treatment may be performed by any types of conventional centrifugal separator, such as Sharples or de Laval centrifuge, but preferably Sharples centrifuge is employed.

The centrifugal force applied is not critical, but is preferably 10G or more, more preferably 50 to 15,000G.

The boron trifluoride-alcohol complex and the desired olefin oligomer are separated by centrifuging the first product, and the recovered boron trifluoride-alcohol complex may be used as the catalyst for the polymerization of the olefin oligomer, without subsequent treatment.

In the step (c), preferably the first product is subjected to one of the moderate treatments (i) to (iii) as in the step (a), before the centrifuging treatment. If the boron trifluoride not included in the complex is removed under the moderate conditions, the first product is not further polymerized during this moderate treatment and the subsequent centrifuging treatment, and thus an oligomer having properly controlled properties can be produced.

According to the present invention, the olefin oligomer can be produced and the catalysts can be recovered.

The oligomer obtained in the present invention usually has a relatively low viscosity, for example, a kinematic viscosity of 2 to 15 cSt at 100° C., a low pour point of, for example, $-50°$ C. or less, a high viscosity index of, for example, 120 or more, and low volatility.

The oligomer obtained in the present invention is useful as synthetic lubricant base fluids, such as an automotive engine oil, a combustion turbine engine oil, an aircraft hydraulic fluid oil, an insulating oil, or the like. The olefin oligomer may be hydrogenated to prepare excellent synthetic lubricants.

EXAMPLES

The present invention now will be further illustrated by, but is by no means limited to, the following Examples.

EXAMPLE 1

Boron trifluoride-n-butanol complex (1.1 ml) and 1-decene (100 ml) were charged into a polymerizer flack equipped with a stirrer, a condenser, a thermometer and a gas-inlet tube, after the inner atmosphere of the flask was replaced with dried nitrogen gas. After cooling to 20° C., a boron trifluoride gas was blown into the flask to initiate polymerization, and the polymerization was performed for 2 hours while the temperature of the flask was maintained at 20° C. by cooling. After the polymerization was completed, dried nitrogen gas was blown into the product for 30 minutes to remove boron trifluoride gas therefrom, and after the blowing was finished, the product was allowed to stand. The boron trifluoride-alcohol complex began to separate and form a lower layer about 1 hour later, and the complex was completely separated after about 2.5 hours. The upper layer was then removed from the flask. Thereafter, using the remaining complex after adding thereto a fresh complex in an amount corresponding to that of the complex dissolved in the upper layer, the above procedure was repeated five times, and each of the resulting upper layers was neutralized with 5% aqueous ammonia, washed with water and dried, and the unreacted olefin monomer and low molecular weight oligomer were evaporated, whereby the desired olefin oligomer was obtained. The yields and properties of the obtained oligomers are shown in Table 1.

EXAMPLE 2

The procedure described in Example 1 was repeated, except that the boron trifluoride gas was removed by stirring the product at a room temperature under 100 mmHg for 1 hour, and the polymerization was repeated three times. The yields and properties of the obtained oligomers are shown in Table 1.

COMPARATIVE EXAMPLE

The procedure described in Example 1 was repeated, except that the boron trifluoride gas was not removed and the product was allowed to stand. The boron trifluoride alcohol complex began to separate after about 3 hours, and was completely separated after about 12 hours. The polymerization was repeated three times, using the resulting catalysts, and the yields and properties of the obtained oligomers are shown in Table 1.

TABLE 1

| Properties of olefin oligomer | Example 1 | | | | | Example 2 | | | Comparative Example 3 | | |
|---|---|---|---|---|---|---|---|---|---|---|---|
| | 1st run | 2nd run | 3rd run | 4th run | 5th run | 1st run | 2nd run | 3rd run | 1st run | 2nd run | 3rd run |
| Yield (%) | 98.7 | 98.6 | 98.2 | 98.2 | 98.5 | 98.6 | 98.8 | 98.5 | 92.1 | 90.3 | 88.7 |

TABLE 1-continued

| Properties of olefin oligomer | Example 1 | | | | | Example 2 | | | Comparative Example 3 | | |
|---|---|---|---|---|---|---|---|---|---|---|---|
| | 1st run | 2nd run | 3rd run | 4th run | 5th run | 1st run | 2nd run | 3rd run | 1st run | 2nd run | 3rd run |
| Number average molecular weight Mn | 560 | 520 | 550 | 540 | 530 | 550 | 540 | 530 | 560 | 540 | 490 |
| Kinematic viscosity at 100° C. (cSt) | 5.843 | 5.190 | 5.773 | 5.494 | 5.458 | 5.636 | 5.494 | 5.467 | 5.853 | 5.773 | 4.673 |
| Viscosity index VI | 143 | 142 | 143 | 142 | 141 | 142 | 142 | 143 | 142 | 142 | 137 |

EXAMPLE 3

After the polymerization was carried out as in Example 1, the upper portion of the condenser on the polymerizer flask was connected with a gas-inlet tube of a gas-absorption flask having a stirrer and containing 50 ml of n-butanol. The polymerizer flask was heated to 160° C. and maintained thereat for 3 hours, while the gas absorption flask was cooled with ice water. After cooling the polymerizer flask, dried nitrogen gas was introduced through the gas-inlet tube thereof, to thereby force the boron trifluoride gas into the gas absorption flask. The changes of weight of the polymerizer flask and the gas-absorption flask, and an analysis of the n-butanol, show that almost all of the complex was separated, absorbed, and then reproduced as the n-butanol complex. The boron trifluoride was blown into the gas-absorption flask to remedy the shortage thereof, whereby the whole was converted to a boron trifluoride-n-butanol complex. The resulting complex (1.1 ml) was used to repeat the above polymerization twice, and the resulting olefin oligomer was finished as in Example 1. The yields and properties of the obtained oligomers are shown in Table 2.

EXAMPLE 4

The procedure described in Example 3 was repeated, except that the boron trifluoride gas was removed as in Example 1. The yields and properties of the obtained oligomers are shown in Table 2.

TABLE 2

| Properties of olefin oligomer | Example 3 | | Example 4 | |
|---|---|---|---|---|
| | 1st run | 2nd run | 1st run | 2nd run |
| Yield (%) | 98.8 | 98.7 | 98.8 | 98.8 |
| Number average molecular weight Mn | 560 | 550 | 550 | 560 |
| Kinematic viscosity cSt at 100° C. | 5.829 | 5.638 | 5.763 | 5.856 |
| Viscosity index VI | 143 | 142 | 143 | 143 |

EXAMPLE 5

After the polymerization was carried out as in Example 1, the polymerization product was charged into a centrifuge tube and centrifuged for 30 minutes at 3,500 rpm (2,200G), using a centrifugal separator (05P-21B; Hitachi Koki K.K.). The upper layer was taken out of the tube, and the complex in the lower layer was charged into the polymerizer flask, to which 100 ml of 1-decene was introduced, and polymerization was carried out five times as above, using the complexes recovered as above. Each of the resulting upper layers was neutralized with 5% aqueous ammonia, washed with water and dried, and the unreacted olefin monomer and low molecular weight oligomer were evaporated and thus, the desired olefin oligomer was obtained. The yields and properties of the obtained oligomers are shown in Table 3.

TABLE 3

| Properties of olefin oligomer | Example 5 | | | | |
|---|---|---|---|---|---|
| | 1st run | 2nd run | 3rd run | 4th run | 5th run |
| Yield (%) | 98.8 | 98.7 | 98.3 | 98.3 | 98.6 |
| Number average molecular weight Mn | 560 | 530 | 550 | 550 | 530 |
| Kinematic viscosity cSt at 100° C. | 5.850 | 5.200 | 5.775 | 5.495 | 5.459 |
| Viscosity index VI | 144 | 143 | 144 | 143 | 142 |

Although the present invention has been described with reference to specific embodiments, various changes and modifications obvious to those skilled in the art are deemed to be within the spirit, scope and concept of the invention.

We claim:

1. A process for manufacturing an olefin oligomer comprising the steps of:
   polymerizing an olefin monomer in the presence of boron trifluoride and a boron trifluoride-alcohol complex as catalysts, to prepare a first oligomerization product;
   removing said boron trifluoride from said first oligomerization product by placing said first oligomerization product under a reduced pressure, at a temperature of less than about 80° C., to thereby prepare a second oligomerization product; and then
   subjecting said second oligomerization product to a precipitation treatment to separate said boron trifluoride-alcohol complex therefrom.

2. A process for manufacturing an olefin oligomer comprising the steps of;
   polymerizing an olefin monomer in the presence of boron trifluoride and a boron trifluoride-alcohol complex as catalysts, to prepare a first oligomerization product;
   removing said boron trifluoride from said first oligomerization product by blowing an inert gas into said first oligomerization product, at a temperature of less than about 80° C., to thereby prepare a second oligomerization product; and then
   subjecting said second oligomerization product to a precipitation treatment to separate said boron trifluoride-alcohol complex therefrom.

3. A process for manufacturing an olefin oligomer comprising the steps of:
   polymerizing an olefin monomer in the presence of boron trifluoride and a boron trifluoride-alcohol complex as catalysts, to prepare a first oligomerization product;
   removing said boron trifluoride from said first oligomerization product by heating said first oligomerization product at a temperature of less than about 80° C., to thereby prepare a second oligomerization product; and then subjecting said second oligomerization product to a precipitation treatment to separate said boron trifluoride-alcohol complex therefrom.

4. A process for manufacturing an olefin oligomer comprising the steps of:

polymerizing an olefin monomer in the presence of boron trifluoride and a boron trifluoride-alcohol complex as catalysts, to prepare an oligomerization product;

removing said boron trifluoride from said oligomerization product by placing said oligomerization product under a reduced pressure, at a temperature of less than about 80° C.; and centrifuging said oligomerization product under a centrifugal force of at least about 10G, to recover said boron trifluoride-alcohol complex.

5. A process for manufacturing an olefin oligomer comprising the steps of:

polymerizing an olefin monomer in the presence of boron trifluoride and a boron trifluoride-alcohol complex as catalysts, to prepare an oligomerization product;

removing said boron trifluoride from said oligomerization product by blowing an inert gas into said oligomerization product, at a temperature of less than about 80° C.; and centrifuging said oligomerization product under a centrifugal force of at least about 10G, to recover said boron trifluoride-alcohol complex.

6. A process for manufacturing an olefin oligomer comprising the steps of:

polymerizing an olefin monomer in the presence of boron trifluoride and a boron trifluoride-alcohol complex as catalysts, to prepare an oligomerization product;

removing said boron trifluoride from said oligomerization product by heating said oligomerization product at a temperature of less than about 80° C.; and centrifuging said oligomerization product under a centrifugal force of at least about 10G, to recover said boron trifluoride-alcohol complex.

7. A process for manufacturing an olefin oligomer according to claim 1, wherein said reduced pressure is within a range from 0.1 to 200 mmHg.

8. A process for manufacturing an olefin oligomer according to claim 4, wherein said reduced pressure is within a range from 0.1 to 200 mmHg.

* * * * *